United States Patent [19]

Faulk

[11] Patent Number: 5,000,935
[45] Date of Patent: Mar. 19, 1991

[54] TREATMENT METHOD UTILIZING TRANSFERRIN-RADIOIODINE CONJUGATE

[76] Inventor: Ward P. Faulk, 4414 Edinburgh Point, Indianapolis, Ind. 46208

[21] Appl. No.: 437,721

[22] Filed: Nov. 17, 1989

Related U.S. Application Data

[62] Division of Ser. No. 64,939, Apr. 1, 1987, Pat. No. 4,895,714.

[30] Foreign Application Priority Data

Aug. 2, 1985 [GB] United Kingdom ............... 8519457

[51] Int. Cl.[5] .................. A61K 43/00; A61K 37/04; A61K 35/14; C07K 15/14
[52] U.S. Cl. .................................. 424/1.1; 530/394; 530/402; 514/5
[58] Field of Search ............... 424/1.1; 530/394, 402; 514/5

[56] References Cited

U.S. PATENT DOCUMENTS

| 4,332,785 | 6/1982 | Allen et al. | 424/1.1 |
| 4,447,547 | 5/1984 | Allen et al. | 436/543 |

OTHER PUBLICATIONS

Aulbert et al. "Uptake of $^{131}$I-Transferrin in Tumor and Liver Tissue" Naturwissenschaften, 1987–68(4) 212–213 [C.A. vol. 94, p. 188091, 1981].

*Primary Examiner*—John S. Maples
*Attorney, Agent, or Firm*—Armstrong, Nikaido, Marmelstein, Kubovcik & Murray

[57] ABSTRACT

Conjugates of transferrin with a radioactive isotope of iodine are utilized to treat cancer in animals.

4 Claims, 8 Drawing Sheets

FIG.12a

TREATMENT METHOD UTILIZING TRANSFERRIN-RADIOIODINE CONJUGATE

This is a division of application Ser. No. 64,939 filed Apr. 1, 1987, and which issued as U.S. Pat. No. 4,895,714 on Jan. 23, 1990.

This invention relates to protein conjugates for use in tumour diagnosis, imaging, localization or treatment.

Transferrin is a protein which occurs in blood plasma, including human blood plasma, and which has an important function in the transport of iron. The role of transferrin and transferrin receptors on reticulocytes has been widely studied.

It has been noted recently that transferrin receptors are to be found on the surface of leukemia and lymphoma cells (Yeh, Taylor and Faulk, Vox Sanguinis, 1984, Vol. 46, page 217). It has been suggested that research into breast cancer diagnosis and therapy might be approached through the use of transferrin labelled with cytotoxic agents (Faulk et al, The Lancet, Aug. 23, 1980, page 392).

A favoured approach to producing tumour imaging agents has involved the linking of radioactive isotopes such as $^{125}I$ to antibodies against tumour-associated surface antigens. The ability of such complexes to localise malignant cells selectively has, so far, been limited. An alternative, and more recent approach has been to use nuclear magnetic resonance, but this approach requires very expensive equipment. Another new approach is positron emission tomography.

Following the identification of transferrin receptors on the surfaces of tumour cells by Faulk and Galbraith (Proc. Roy. Soc. (B) 204: 83-97, 1979), Trowbridge and Domingo (Nature, Vol. 294, page 171, 1981) have obtained monoclonal antibodies against the transferrin receptor of human cells, and have coupled such antibodies to ricin or diphtheria toxin sub-units. They found that the antibody bound to human tumour cells as evidenced by the inhibition of cell growth in vitro caused by such conjugates. However, in experiments designed to test the effectiveness of the antibody-toxin conjugates in vivo, they found that anti-transferrin receptor antibody alone inhibits the growth of human melanoma cells in nude mice. They found no evidence that the conjugate is more effective than unmodified antibody in inhibiting growth of M21 melanoma cells in nude mice. That is to say, the cytotoxic properties of the ricin A moiety of the antibody-toxin conjugate were not manifest in vivo. It is essential that convincing in vivo data be put forward to support new methods of tumour diagnosis, localization, imaging or treatment.

Further teaching regarding such monoclonal antibodies can be found in U.S. Pat. No. 4,434,156.

In contrast to the results of Trowbridge and Domingo, it has been found that when an anti-tumour agent is conjugated with transferrin, not only does the protein moiety retain its affinity for transferrin receptors, but, moreover, the anti-tumour agent retains its anti-tumour properties (Yeh and Faulk, Clin. Imm. Immunopath., 1984, Vol. 32, pages 1-11). In this connection the reader is referred also to GB-B-2116979, to WO85/00812, and to EP-A-0134320.

Preparation of $^{113}In$-transferrin aggregates is described in DE-A-2108528, in DE-A-2150000 and in U.S. Pat. No. 3,939,258. $^{103}Ru$-labelled transferrin is disclosed in U.S. Pat. No. 4,448,762. A complex of radioactive gallium and transferrin is proposed as a component of a radiopharmaceutical composition in claim 20 of U.S. Pat. No. 4,448,763. In such aggregates and complexes the metal atom is chelated by the transferrin molecule.

Although such aggregates and complexes are proposed for use in radiodiagnosis, the radioactive metal is generally relatively loosely bound in the complex or aggregate by the chelating action of the protein and can be released from the complex or aggregate in vivo into the bloodstream. Hence the desired specificity of binding may be less than optimal and the presence of the free metal ions in the bloodstream may give rise to undesirable side effects.

Binding of $^{125}I$-transferrin to purified human transferrin receptor is mentioned in U.S. Pat. No. 4,332,785 but no description is given of its method of preparation.

A product which is designated as "Transferrin, human [$^{125}I$]" is listed under the reference NEX-212 in the 1985/1986 Research Products catalogue of New England Nuclear, effective Apr. 14, 1985. This is described as containing $0.1-1.0\mu$ Ci/$\mu$g of radioactivity and as having a molecular weight of about 80,000. No specific use is suggested for this product by its manufacturers. Although in vitro experiments, including radioimmunoelectrophoresis, indicate that this product has antigenic properties, as measured by its capacity to be recognised by rabbit antibodies to human transferrin and to be coprecipitated by sheep antibodies to rabbit immunoglobulins, the product exhibits by autoradiography on gel many radio-labelled contaminants and what appear to be radio-labelled breakdown products. Moreover it shows indifferent characteristics as a tumour imaging agent in vivo experiments and there is no evidence to show that it is localized in vivo at the site of a tumour. Hence it is unsuitable for use as a tumour imaging agent, presumably because of contaminants, breakdown products and an alteration in the characteristics of the protein moiety of the conjugate in the course of the preparation of the conjugate which disallow in vivo use and affect adversely the binding of the conjugate with transferrin receptors. Hence it would appear that it is misleading to refer to this commercially available material as a conjugate of transferrin as its properties do not retain all of the in vivo characteristics of transferrin.

It is an object of the present invention to provide movel protein conjugates for use in tumour diagnosis, imaging, localization or treatment.

It is a further object of the invention to provide movel conjugates of transferrin for use as tumour diagnostic, imaging, localization or treatment agents.

According to the present invention, there is provided a conjugate of transferrin with a radioactive isotope of iodine for use in tumour diagnosis, imaging, localization or treatment. Such a conjugate comprises molecules of transferrin labelled with a radioactive isotope of iodine. It can be prepared by introducing the selected isotope into transferrin by a suitable labelling process. The resulting labelled transferrin conjugate will often contain unlabelled transferrin molecules in addition to the desired labelled transferrin molecules. As the labelling process will often give rise to aggregates and/or fragments of the labelled and/or unlabelled transferrin molecules, these are usually best removed from the resulting crude reaction product prior to in vivo use. Otherwise such aggregates and/or fragments may interfere with the desired isotopically labelled transferrin conjugate.

The radioactive isotope of iodine may be, for example, $^{125}$I or $^{131}$I.

Preferably the transferrin used in making the conjugate is apotransferrin (i.e. the iron-free form of transferrin).

The invention further provides a process for producing a conjugate of transferrin with a radioactive isotope which comprises the steps of labelling transferrin with a radioactive isotope of iodine by contact with a source of that isotope in the presence of a suitable coupling agent, and subsequently separating the labelled conjugate of native transferrin from conjugates comprising aggregated protein molecules or fragments of protein molecules. Such aggregates and fragments include aggregates and fragments of isotopically labelled or unlabelled transferrin molecules.

In one labelling method one or more atoms of the desired isotope (e.g. $^{125}$I-atoms) is or are introduced into the transferrin molecule by an oxidative method. For example, chloramine-T can be used in conjunction with a source of $^{125}$I, such as $^{125}$I-labelled NaI. However, such a technique tends to produce a relatively high proportion of aggregates and/or fragments of labelled and unlabelled transferrin. It is accordingly preferred to use a more gentle-acting oxidative coupling agent, such as lactoperoxidase. Although the exact structure of the resulting conjugates has not been investigated, it is believed that, in the presence of the oxidising agent, atoms of iodine become covalently bound to the transferrin molecules, possibly as substituents or the benzene ring of aromatic amino acids present in transferrin. Aromatic amino acids include phenylalamine and tyrosine.

The invention also provides a conjugate of transferrin with $^{125}$I which is substantially free from aggregates and/or fragments of isotopically labelled or unlabelled transferrin. Such a conjugate preferably contains from about $0.5 \times 10^6$ cpm to about $2 \times 10^6$ cpm $^{125}$I per microgram of transferrin. (The abbreviation "cpm" means counts per minute). Preferably the transferrin with which the $^{125}$I is conjugated is apotransferrin (i.e. the iron-free form of transferrin).

The invention further provides a process for forming a conjugate of transferrin with $^{125}$I which comprises effecting conjugation of transferrin with a source of $^{125}$I so as to introduce into the resulting conjugates from about $0.5 \times 10^6$ cpm to about $2 \times 10^6$ cpm of $^{125}$I per microgram of transferrin, and subsequently separating the resulting conjugate of native transferrin from conjugates comprising aggregated protein molecules or fragments of protein molecules.

It is preferred that the transferrin be linked to the $^{125}$I by means of lactoperoxidase.

The transferrin is preferably of human origin, though any transferrin may be used which can bind to transferrin receptors on the surface of the tumour cell which it is desired to locate.

For in vivo use, the transferrin conjugate is preferably separated from conjugates which comprise aggregated transferrin molecules and/or aggregates or fragments of transferrin molecules created by the labelling process. Such aggregates and/or fragments may be separated from the desired conjugates by, for example, gel filtration chromatography. This also separates unbound isotope from the conjugates, though most free isotopes can be partitioned from transferrin-bound isotope by simple dialysis.

The invention additionally provides a tumour diagnostic, imaging, localization or treatment agent comprising a conjugate of transferrin with a radioactive isotope of iodine such as $^{125}$I, according to the invention.

According to a further aspect of the present invention there is provided a reagent kit for the diagnosis, location, imaging and treatment of tumours comprising transferrin and a conjugate of transferrin with a radioactive isotope of iodine, such as $^{125}$I, according to the invention.

When the tumour is located, imaged and diagnosed, it can also be treated by using conjugates of transferrin with anti-tumour agents such as adriamycin, as described in GB-B-2116979, in WO85/00112 or in EP-A-0134320. Such of the patient's normal cells which have transferrin receptors may be protected against the effects of the conjugates by saturating these receptors with iron-bearing transferrin before administration of the conjugate. The uptake of radioactive iodine by normal tissues such as thyroid can be blocked with the use of thyroid blocking drugs or by simply pre-loading the test subject with iodine. Both are well known, widely used, safe, standardized procedures, both have been used in laboratory animals in the testing of the tumour imaging agents of the present invention.

BRIEF DESCRIPTION OF THE DRAWINGS

FIGS. 12a and 12b are tracings on X-ray film of the mouse in FIG. 2 imaged 220 hours after intraperitoneal injection of $^{125}$I-apotransferrin with and without a collimator.

There are now described, by way of example, a conjugate of transferrin with $^{125}$I according to the present invention, and a method for preparing the same, with reference to the following three experiments.

EXPERIMENT I: LABELLING OF TRANSFERRIN WITH $^{125}$I

A $^{125}$I conjugate of human transferrin was prepared by incubation of 5 micrograms of human apotransferrin from Sigma (St. Louis, U.S.A.) with 1.2 mC of $^{125}$I in the form of NaI for 20 minutes at room temperature in the presence of Bio-Rad Enzymobeads (Bio-Rad, Richmond, Calif.) in phosphate buffer (pH 7.2) which also contained BD-glucose. The reaction was stopped by adding Tris-HCl buffer (pH 7.4) and albumin. According to the manufacturers' literature Bio-Rad Enzymobeads are a solid phase form of lactoperoxidase/glucose oxidase. The resulting conjugate was dialyzed with phosphate buffer and then for 24 hours at 5° C. with three changes of a 1000-fold excess of sterile saline (0.01M, pH 7.4) to remove unconjugated isotope. Following dialysis, scintillation counting showed that $5 \times 10^6$ counts per minute (cpm) of $^{125}$I was bound to the transferrin (i.e. $1 \times 10^6$ cpm of $^{125}$I per microgram of transferrin). It is possible to prepare conjugates of higher specific activity, but with the tumour imaging equipment employed in the following example it was preferable to use these concentration counts per minute, for this gives more precise tumour localization. Other controls for imaging of available emission in radioactive transferrin conjugates are available within the scanning technology, such as (a) whether the irradiation beams are parallel or parallex, (b) the intensity setting of the machine, and (c) the number of counts to which the X-ray film is exposed. Examples of these variables are presented in the Example below.

EXPERIMENT II: RETAINED ANTIGENICITY OF LABELLED TRANSFERRIN

With the use of radio-immunoelectrophoresis as described by Faulk, Karam and Fudenberg (J. Immunol. 106: pp. 1112-1116, 1971) for iodine isotopic conjugates of insulin, it was shown that the $^{125}$I-transferrin conjugate from Experiment I retained its antigenic properties as measured by the capacity to be recognised by rabbit antibodies to human transferrin and co-precipitated by sheep antibodies to rabbit immunoglobulins.

Figure 1:
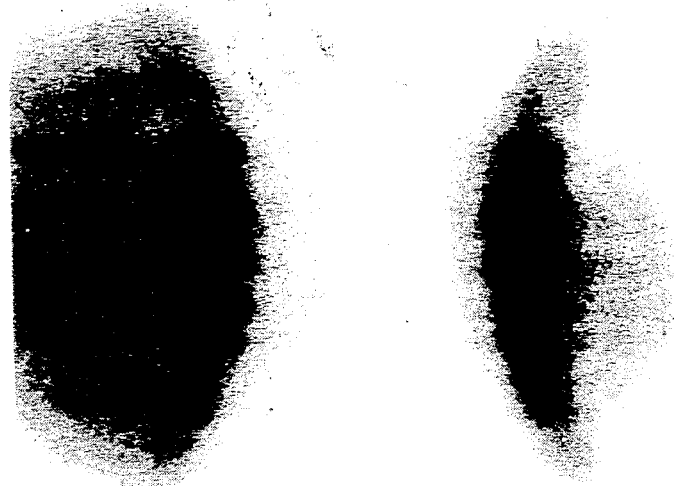
FIG. 1 shows the result obtained when the $^{125}$I-apotransferrin conjugate of the present invention is subjected to electrophoresis.

FIG. 1 shows the result of radio-immunoelectrophoresis for the $^{125}$I-transferrin conjugate.

EXPERIMENT III: RETAINED RECEPTOR RECOGNITION OF LABELLED TRANSFERRIN

With the use of indirect immunofluorescence as described for many antigens by Faulk and Hijmans (Prog. Allergy. 16: pp. 9-39, 1972) and for the ability of transferrin antigens to be bound by human transferrin receptors on human tumour cells (Yeh and Faulk, Clin. Immunol. Immunopathol., Vol. 32, pp. 1-11, 1984) it was shown that the $^{125}$I-transferrin conjugate was recognised and bound by transferrin receptor-bearing human tumour cells.

The above three in vitro experiments show that isotope conjugates of human transferrin fulfil the criteria for the development of a transferrin receptor-mediated assay in vivo for the localization, imaging and possible treatment of transferrin receptor-bearing tumour cells. These criteria are: (a) transferrin can be labelled with tracer/treater isotopes; (b) the labelled transferrin retains its antigenicity, and (c) the labelled transferrin retains its ability to be recognised and bound by transferrin receptor-bearing tumour cells. Results from in vivo experiments are given in the following example.

EXAMPLE

The design of this example is to show that the conjugate of $^{125}$I-transferrin remains significantly longer in tumour-bearing laboratory animals than in animals without tumours. Similarly, the conjugate remains in vivo longer than does the isotope alone. More importantly, by using standard tumour imaging equipment, it will be shown that the conjugate is located within the tumour.

To avoid the uptake of iodine by iodine utilizing tissues such as thyroid, the animals were given iodine in their drinking water for two days before and during the experiments.

To avoid the uptake of apotransferrin conjugates into transferrin receptors on normal cells such as reticulocytes, the animals were given ferric ions in the form of ferric sulphate added to their drinking water for two days before and during the experiments.

To avoid the mounting of an immune response in the mice given isotopic conjugates of human transferrin, immunologically deficient animals (nude mice) were used. However, the mounting of an immune response was not found to be a problem inasmuch as immunologically competent animals (Swiss white mice) produced similar results to nude mice when given isotopic conjugates of human transferrin.

To avoid the possibility that differing routes of administration of the $^{125}$I-transferrin conjugates could produce different results in tumour imaging, both intravenous and intraperitoneal routes were investigated. This does not appear to be an important variable in the experiments, inasmuch as no significant differences between these injection routes were detected. In this example, only results from intraperitoneal injections into nude mice are presented.

Nude mice were injected subcutaneously with $20 \times 10^6$ K562 cells. These human cells have been shown to have plasma membrane-bound receptors for transferrin. Three weeks later, tumours were visible at the injection sites. For purposes of example, a representative animal will be presented with supporting tumour-imaging photographs.

Figure 2:
FIG. 2 is a photograph of a mouse having a posteriolaterally positioned tumor.

A tumour measuring 10 mm in diameter and standing 15 mm high was apparent posterio-laterally three weeks after the injection of K562 cells (FIG. 2). The mouse was 40 mm long.

Figure 3:
FIG. 3 is a tracing on X-ray film of the mouse in FIG. 2 imaged 8 hours after intraperitoneal injection of $^{125}$I-apotrasferrin.

The animal was injected intraperitoneally with a lactoperoxidase prepared conjugate of $^{125}$I-transferrin containing 5 $\mu$ grams apotransferrin and $5 \times 10^6$ cpm of $^{125}$I. Eight hours later the mouse was imaged for 10,000 counts by using an image analyzer fitted with a collimator and the tracing was developed on X-ray film. The machine was standardized at an intensity setting of 800. The result (FIG. 3) was essentially that obtained from a blood pool study done on control nude or Swiss white mice who were not injected with K562 cells.

Figure 4A:
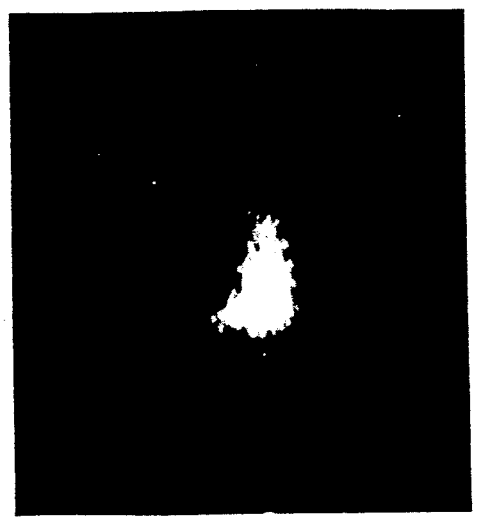
FIG. 4a is a tracing on X-ray film of the mouse in FIG. 2 imaged 32 hours after intraperitoneal injection of $^{125}$I-apotrasferrin.
Figure 4B:
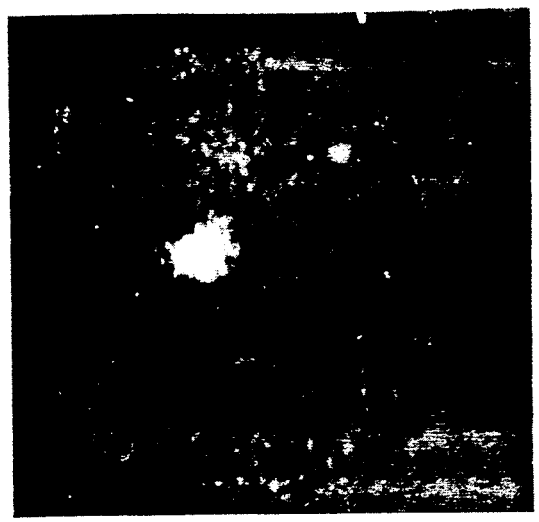
FIG. 4b is a tracing similar to 4a but with the blood pool shielded with a lead apron.

Thirty-two hours after injection of conjugate, the tumour could be distinguished from the blood pool distribution of radio labelled conjugate. This appeared as a posterio-lateral protruding mass (FIG. 4a). When the distribution of blood pool was shielded with a lead apron, the dimensions of the K562 tumour were visualised (FIG. 4b).

Figure 5:
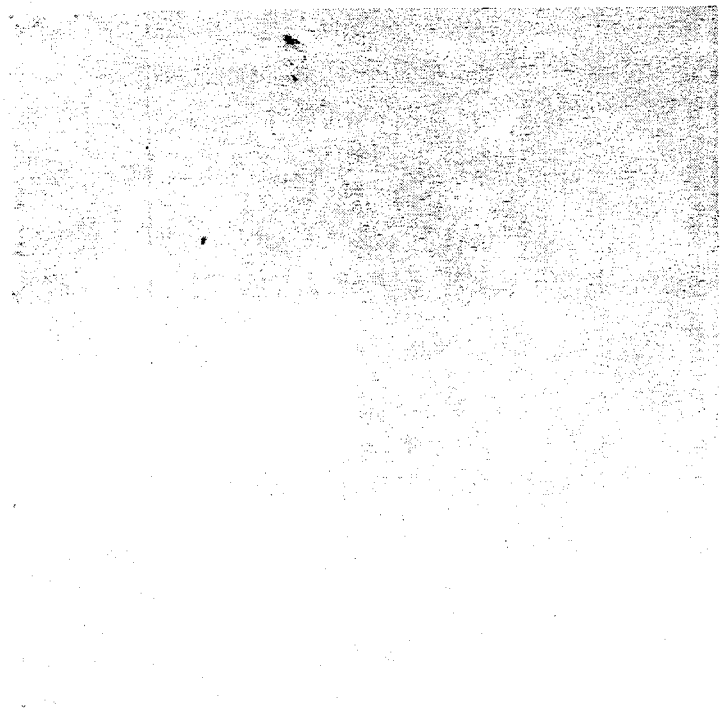
FIG. 5 is a tracing on X-ray film of the mouse in FIG. 2 imaged 56 hours after intraperitoneal injection of $^{125}$I-apotransferrin.

Fifty-six hours after injection of conjugate, two major changes were noted. Firstly, the blood pool distribution was less extensive and appeared as an abdominal mass which was shown by necropsy and radioactive organ counting in parallel test animals to be largely liver and gut. Secondly, the tumour could easily be distinguished from the abdominal mass as a larger posterior mass (FIG. 5).

Figure 6:
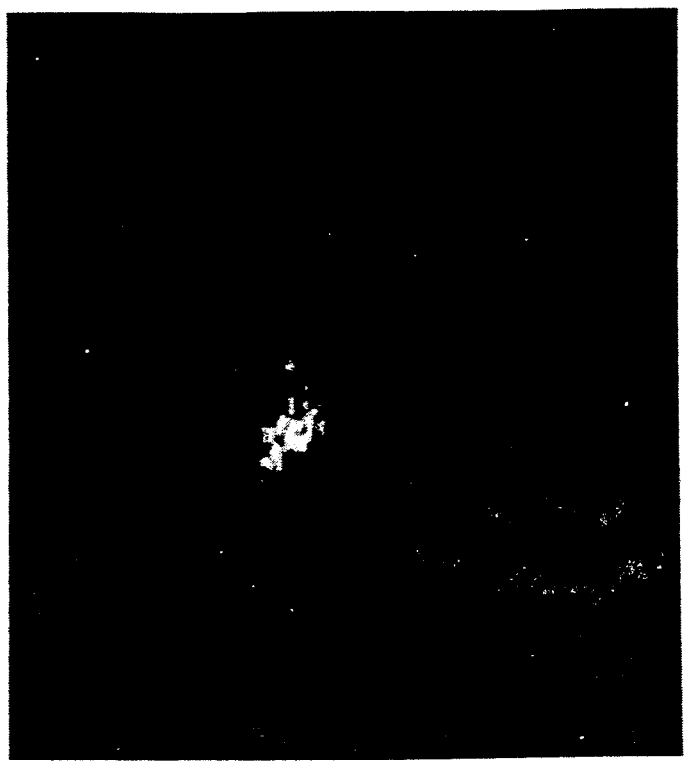
FIG. 6 is a tracing on X-ray film of the mouse in FIG. 2 imaged 75 hours after intraperitoneal injection of $^{125}$I-apotransferrin.

Seventy-eight hours after injection of conjugate, the abdominal mass had cleared and the K562 tumour remained as an area of intense radioactivity (FIG. 6). At this time, there was no localized focus of irradiation from control animals who received conjugate without having received a prior injection of K562 cells. The total body emission from control animals was so low as to be barely detectable by X-ray film.

Figure 7:
FIG. 7 is a tracing on X-ray film of the mouse in FIG. 2 imaged 100 hours after intraperitoneal injection of $^{125}$I-apotransferrin.

One hundred hours after injection of conjugate, it was not possible to record emission from control animals, yet the tumour in the test mouse was clearly visualised (FIG. 7). In this case the mass appeared as two foci. Histopathological studies done in other test animals showed a central necrosis of the cancer and compromised circulation to the core, probably accounting for the two foci noted in FIG. 7. The control was negative in all subsequent experiments.

Figure 8A:
FIG. 8a is a tracing on X-ray film of the mouse in FIG. 2 imaged 124 hours after intraperitoneal injection of $^{125}$I-apotransferrin.
Figure 8B:
FIG. 8b is a tracing on X-ray film of the urine excreted by the mouse 124 hours after intraperitoneal injection of $^{125}$I-apotransferrin.

One hundred and twenty-four hours after injection of conjugate, the tumour is still detectable giving a good cross-sectional localization of the mass when the image analyzer's collimator is in place (FIG. 8a). However, when the collimator is removed, and the mouse is placed over the detection crystal, it is possible to image the entire animal as well as a pool of radioactive urine passed during the counting procedure (FIG. 8b, urine marked as "contamination"). It should be noted that the contamination is imaged when the emission beams are viewed in parallex; with the collimator in place, the beams are made parallel and the tumour is seen, though the urinary contamination appears as a front image in the lower right quadrant of FIG. 8b.

Figure 9A:
FIGS. 9a–d are tracings on X-ray film of the mouse in FIG. 2 imaged 1148 hours after intraperitoneal injection of $^{125}$I-apotransferrin using a collimator, with the mouse directly on the detection crystal using 10,000 counts, with the mouse on the detection crystal using 5000 counts, and using a collimator and placing a lead apron over the non-tumor bearing areas of the mouse.
Figure 9D:
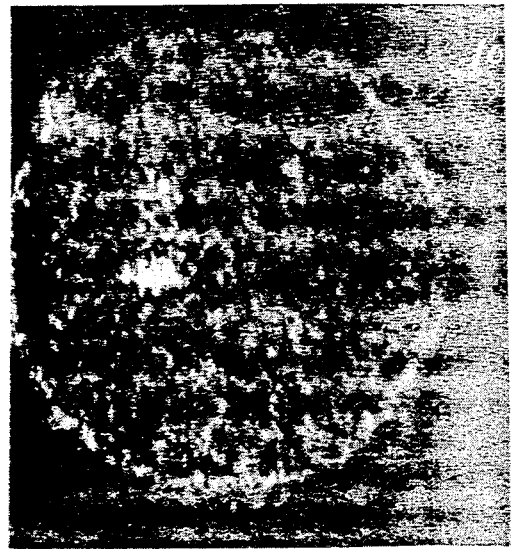
Figure 9B:
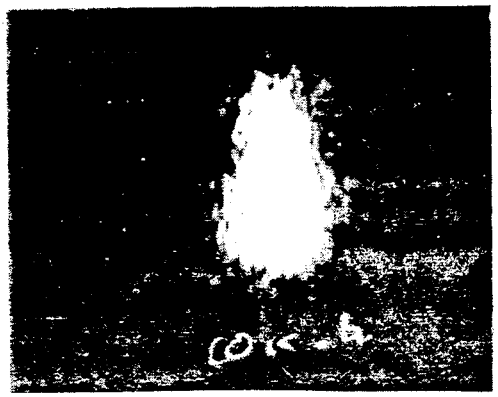
Figure 9C:

One hundred and forty-eight hours after injection of conjugate, the tumour was clearly identified with the collimator in place (FIG. 9a). However, the residual body and blood pool irradiation was so intense that it was not possible to scan 10,000 counts with the animal directly on the detection crystal (FIG. 9b). This procedure was also disallowed for scanning 5000 counts directly on the crystal (FIG. 9c). With the collimator in place, the tumour could be coned in by placing a lead apron over the non-tumour bearing areas (FIG. 9d).

Figure 10B:
FIGS. 10a–d are tracings on X-ray film of the mouse in FIG. 2 imaged 172 hours after intraperitoneal injection of $^{125}$I-apotransferrin without a collimator, with a collimator using 50,000 counts and without a collimator using 100,000 counts at two different settings.
Figure 10A:
Figure 10C:
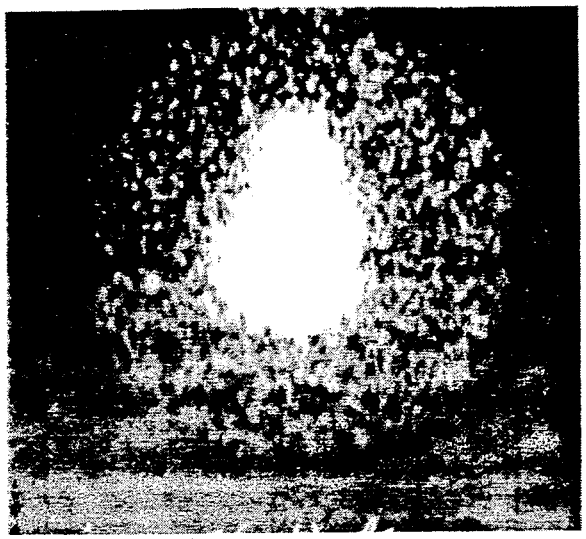
Figure 10D:

One hundred and seventy-two hours after injection of conjugate, the mouse was rapidly scanned for parallex emission without collimator (FIG. 10a). It can be noted that at this time using an exposure of 10,000 counts at an intensity of 800, the body and blood pool irradiation still present an impediment to tumour localization. However, residual irradiation was completely eliminated from imaging with the collimator, and the malignancy was clearly seen (FIG. 10b). The importance of the number of counts to which the X-ray film is exposed is illustrated by removing the collimator and increasing the usual 10,000 counts to 50,000 counts (FIG. 10c). With the use of these conditions it is not possible to image the tumour. The importance of the intensity setting of the machine is illustrated by lowering the usual 800 setting to 500 while increasing the counts to 100,000 without the collimator (FIG. 10d). It will be noted that under these conditions the tumour can be imaged without the collimator (compare with FIG. 10a). Clearly, precise tumour imaging depends not only on the specific activity of the conjugate, but also on the geometric orientation of the emission beam, the number of counts to which the X-ray film is exposed and the intensity setting of the machine. However, none of these variables is important if the tumour imaging agent is not bound by receptors on the tumour cell surface. Illustrations in this in vivo example support data from in vitro experiments that $^{125}$I-transferrin is bound by transferrin receptors on the tumour cell surface.

Figure 11B:
FIGS. 11a–d are tracings on X-ray film of the mouse in FIG. 2 imaged 196 hours after intraperitoneal injection of $^{125}$I-apotransferrin under the same conditions as in FIGS. 10a–d.
Figure 11A:
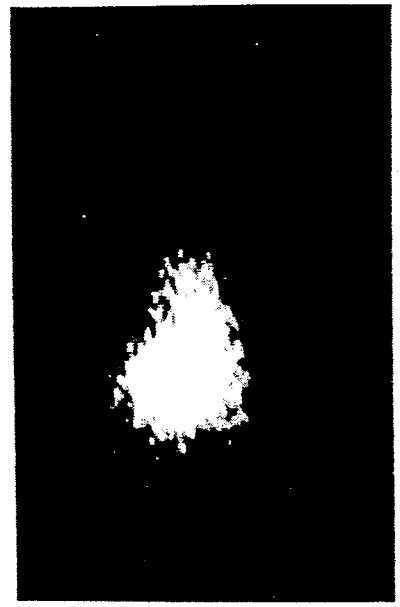
Figure 11C:
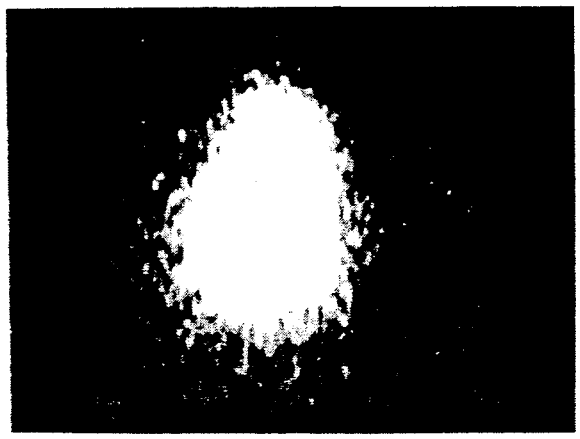
Figure 11D:
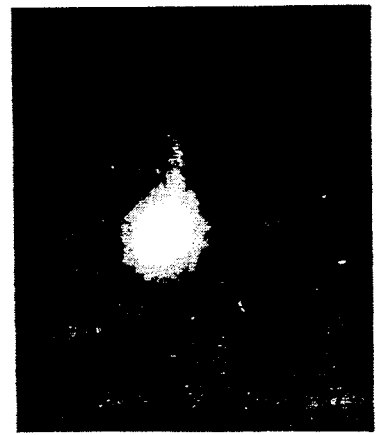

One hundred and ninety-six hours after injection of conjugate, the mouse was studied at the same variable settings as presented in FIGS. 10a, b, c and d. The tumour was not well visualized without collimator (FIG. 11a) but was located and imaged with collimator by using the same number of counts (i.e. 10,000) (FIG. 11b). Too much irradiation is recorded without the collimator after 50,000 counts with an intensity of 800 (FIG. 11c), though good localization was recorded without collimator after 100,000 counts with an intensity setting of 500 (FIG. 11d).

Two hundred and twenty hours after injection of conjugate, the tumour was barely visible with collimator in place and the usual determinants of 15,000 counts and 800 intensity (FIG. 12a) but it was still imagable without collimator at the same number of counts and intensity (FIG. 12b). The mouse also was scanned at 244, 268, 292 and 316 hours after injection of $^{125}$I-transferrin conjugate by using the collimator for 15,000 counts at an intensity of 800; the results were a gradual diminishment of the tracing presented in FIG. 12a. However, even at 316 hours after conjugate injection the tumour was rapidly visualized without the collimator by using either 10,000 counts at 800 intensity or 50,000 or 100,000 counts at 500 intensity.

A post mortem examination of a similar mouse 72 hours after injection of $^{125}$I-transferrin conjugate gave the following results:

| Tissues | cpm |
| --- | --- |
| 1. Submaxillary glands | 12976 |
| 2. Spleen | 7389 |
| 3. Rib cage and sternum | 9039 |
| 4. Left and right kidneys | 26576 |
| 5. Liver | 71964 |
| 6. Heart | 11948 |
| 7. Lungs | 15878 |
| 8. Bladder and male tubes | 5208 |
| 9. Thyroid and larynx | 72121 |
| 10. Stomach | 14633 |
| 11. Small intestine | 48589 |
| 12. Large intestine to caecum | 10577 |
| 13. Caecum | 14637 |
| 14. Brain | 1196 |
| 15. Stomach contents | 14831 |
| 16. Muscle mass (thigh) | 5092 |
| 17. Tumour | 266766 |
| 18. Tumour | 338085 |
| 19. Tumour | 156448 |
| 20. Tumour | 226963 |
| 21. Unknown mass close to liver | 17809 |

The unknown mass (item 21) was clearly not a tumour metastasis.

I claim:

1. A method of treating a subject suffering from cancer which comprises administering to the subject a pharmacologically effective amount of a conjugate of a transferrin with a radioactive isotope of iodine.

2. A method according to claim 1, where the radioactive isotope of iodine is $^{125}$I.

3. A method according to claim 1, wherein the transferrin is apotransferrin.

4. A method according to claim 3, wherein the radioactive isotope of iodine is $^{125}$I.

* * * * *